(12) United States Patent
Sarma et al.

(10) Patent No.: US 8,680,288 B2
(45) Date of Patent: Mar. 25, 2014

(54) PYRIDIN-2YL SULFANYL ACID ESTERS AND PROCESS FOR THE PREPARATION THEREOF

(75) Inventors: Jadab Chandra Sarma, Assam (IN); Dilip Chandra Bora, Assam (IN); Paruchuri Gangadhar Rao, Assam (IN); Balaram Ghosh, New Delhi (IN); Sakshi Balwani, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/811,090

(22) PCT Filed: Jul. 20, 2011

(86) PCT No.: PCT/IN2011/000477
§ 371 (c)(1),
(2), (4) Date: Jan. 18, 2013

(87) PCT Pub. No.: WO2012/011123
PCT Pub. Date: Jan. 26, 2012

(65) Prior Publication Data
US 2013/0131350 A1 May 23, 2013

(30) Foreign Application Priority Data
Jul. 20, 2010 (IN) .......................... 1691/DEL/2010

(51) Int. Cl.
*C07D 213/62* (2006.01)
*A61K 31/435* (2006.01)

(52) U.S. Cl.
USPC .......................................... 546/301; 514/277

(58) Field of Classification Search
USPC ....................................................... 546/301
See application file for complete search history.

(56) References Cited

U.S. PATENT DOCUMENTS 5,998,456 A 12/1999 Aoki et al.
6,777,432 B1 8/2004 Cutshall et al.

OTHER PUBLICATIONS

Beugelmans R. et al., "Action De Sulfanions Sur Les Halogenures D'Aryle Fonctionnalises, Synthese Directe De Benzothiophenes et Thienopyridines," Tetrahedron, Elsevier Science Publishers, Amsterdam, NL, vol. 39, No. 24, Jan. 1, 1983, pp. 4153-4161.
Kohra et al., "Reaction of 2-Trimethylsilymethylthiopyridine Promoted by a Fluoride Ion: The First Example of Generation of 2-Pyridylthiomethylcarbanion," Heterocycles, Elsevier Science Publishers B.V. Amsterdam, NL, vol. 36, No. 7, Jan. 1, 1993, pp. 1497-1500.
David Crich et al., Some Studies on syn-Elimination Reaction, Journal of Chemical research, Nov. 1987, p. 353.

*Primary Examiner* — John Mabry
(74) *Attorney, Agent, or Firm* — Blank Rome LLP

(57) ABSTRACT

The present invention relates to Pyridin-2-yl sulfanyl acid ester compounds having antiinflammatory properties. The present invention particularly relates to novel anti-inflammatory heterocyclic acid esters of Pyridin-2-yl sulfanyl having the structure of general formula 1 which have been screened for their antiinflammatory activity with respect to inhibition of adhesion of neutrophils, isolated from human peripheral blood, onto the surface of human umbilical vein endothelial cells (HU-VEC) as a result of inhibition of the cytokine-stimulated expression of cell adhesion molecule ICAM-1. The compound RS—Z, 3-(Pyridin-2-yl sulfanyl)-propionic acid pentyl ester (structure 1a, $R_1$=H, $R_2$=H, $R_3$=CH2-COOC5H$_{11}$) was found to be most effective for ICAM-1 and neutrophil adhesion inhibition and was found to effectively alleviate inflammation mediated by excessive leukocyte infiltration leading to inflammatory disorders or like conditions, such as acute lung injury and acute respiratory distress syndrome in mice.

9 Claims, 3 Drawing Sheets

PYRIDIN-2YL SULFANYL ACID ESTERS AND PROCESS FOR THE PREPARATION THEREOF

CROSS-REFERENCE TO RELATED APPLICATIONS

The present application is a national phase of International Patent Application No. PCT/IN2011/000477, filed Jul. 20, 2011, which claims priority to Indian Patent Application No. 1691/DEL/2010, filed Jul. 20, 2010, the entire disclosures of which are incorporated by reference herein.

FIELD OF THE INVENTION

Present invention relates to Pyridin-2-yl sulfanyl acid ester compounds of general formula 1

General Formula 1 wherein
$R_1$=H;
$R_2$=H, COOMe;
$R_3$=(CH2)$_n$COOR$_4$;
$R_4$=C$_2$H$_5$, C$_3$H$_7$, C$_4$H$_9$, C$_5$H$_{11}$, C$_6$H$_{11}$;
n=1-7.

The present invention further relates to the synthesis of acid ester of Pyridin-2-yl sulfanyl compounds of general formula 1 (heterocyclic add esters of pyridine-2-yl sulphanyl or heterocyclic acid esters of 2-pyridinylthio compounds).

Present invention further relates to compounds of general formula 1 exhibiting potent anti-inflammatory activity with respect to inhibition of adhesion of neutrophils isolated from human peripheral blood onto the surface of human umbilical vein endothelial cells (HUVECs) as a result of inhibition of the cytokine-stimulated expression of cell adhesion molecule ICAM-1 (Intercellular cell adhesion molecule-1).

Present invention further relates to the synthesis and use of the most active compound (1a) RS—Z, 3-(Pyridin-2-yl sulfanyl)-propionic acid pentyl ester in mice to alleviate inflammation mediated by excessive leukocyte infiltration leading to inflammatory condition or disorders such as acute lung injury, acute respiratory distress syndrome, septic shock, ischemia-hyperfusion etc.

BACKGROUND OF THE INVENTION

An analysis of the molecular structure of active anti-inflammatory agents available in literature suggests that these compounds contain a sub structure of pyridyl group, acid group and sometimes even a sulfur atom.

Phenylthiomethyl pyridine

Diclonixin

Anpirtoline

Pyridyl carbothiolate

As for example, compounds like phenylthiomethyl pyridine, Diclonixin, Anpirtoline and Pyridyl carbothiolate contain a pyridyl moiety whereas Anpirtoline and Pyridyl Carbothiolate contain sulfur attached directly to the pyridyl moiety. While looking for some novel anti-inflammatory compound we propose to keep the basic pyridyl moiety intact with change in derivatization pattern on the sulfur and the carboxylic acid group.

From the existing literature it is evident that the compound of interest i.e. the most active compound RS—Z (3-(Pyridin-2-yl sulfanyl)-propionic acid pentyl ester (Ia)) is a new compound not prepared or reported before. Similar compounds or compounds bearing at least thiopyridyl substructure reported in literature are also limited. Following compounds have similarity to the compound of interest here.

(A)

(B)

(C)

But none of these compounds are reported to have any biological activity. Compound (A), i.e. 3-(2-pyridylthio) propionic acid ethyl ester has been reported during the course of study on aromatic substitution (Rossi R A, Pierini A B, Santiago A N, Nucleophilic Aromatic Substitution Organic Reactions 1999, 54, Hoboken, N.J., US), addition reaction of electrogenerated thiolate anion to olefin (Niyazymbetov M E, Konyushkin L D, Niyazymbetova Z I, Litvinov V P, Petrosyan V A. Electrocatalytic addition of thiols to activated olefins. Khimicheskaya, 1991, 260), syn-elimination (Crich D, Lim L B L, J. Chem. Research (S), 1987, 353) and study of SRN1 reaction (Beugelmans R, Bois-Choussy M, Boudet B, Etude des reactions de $s_{rn}1$—parte 10: Action de sulfanions sur les halogenures d'aryle fonctionnalises. Synthese directe de benzothiophenes et thienopyridines Tetrahedron, 1983, 39, 4153). Compound (B), i.e. 5-(2-pyridylthio) pentanoic acid methyl ester is reported in a study on radical reactions (Barton H R, Bridon D, Fernandez-Picot I, Zard S Z, Tetrahedron, 1987, 43, 2733). Compound (C), i.e. 4-(2-pyridylthio) butanoic acid ethyl ester is reported in a study on reaction of 2-trimethylsilylmethylthiopyridine with alkene (Kohra S, Ueda H, Tominaga Y. Reaction of 2-trimethylsilylmethylthiopyridine promoted by a fluoride ion: the first example of generation of 2-pyridylthiomethylcarbanion Heterocycles, 1993, 36, 1497). It was reported some time back that few anti-inflammatory compounds of type phenylthiomethyl pyridine possess biological results (Haviv F, DeNet R W, Michaels R J, Ratajczyk J D, Carter G W, Young P R. 2-[(Phenylthio)methyl]pyridine derivatives: new anti-inflammatory agents. *J. Med. Chem.* 1983, 26, 218).

OBJECTIVE OF THE INVENTION

The main objective of the present invention is to provide compounds of general formula 1 having anti-inflammatory activity.

Another object of the present invention is to screen compounds of general formula 1 for their anti-inflammatory activity in in-vitro cell-based assay system.

Yet another object of the present invention is to provide most active compound of formula 1a from the series of the evaluated anti inflammatory compounds.

Still another object of the present invention is to determine the $IC_{50}$ values for the inhibition of ICAM-1 and neutrophil adhesion by anti inflammatory compounds for functional correlation of cytokine-induced expression by the novel anti-inflammatory compounds.

Still another object of the present invention is to evaluate in-vivo efficacy of the selected most active novel anti-inflammatory compound of formula 1a in the mice model of LPS induced acute lung injury.

SUMMARY OF THE INVENTION

Accordingly, present invention provides compound of general formula 1

General Formula 1 wherein
$R_1$=H;
$R_2$=H, COOMe;
$R_3$=(CH2)$_n$COOR$_4$;
$R_4$=$C_2H_5$, $C_3H_7$, $C_4H_9$, $C_5H_{11}$, $C_6H_{11}$;
n=1-7.

In an embodiment of the present invention, representative compounds of general formula 1 are:

3-(2-pyridylthio)propionic acid butyl ester (RS 20);

3-(2-pyridylthio)propionic acid pentyl ester (RS Z);

7-(2-pyridylthio)heptanoic acid ethyl ester (RS 32);

3-(2-pyridylthio)propionic acid cyclohexyl ester (RS 21);

2-(2-pyridylthio)-hexanedioic acid 6-cyclohexyl ester 1-methyl ester (AD 21);

2-(2-pyridylthio)-hexanedioic acid 1-methyl ester 6-propyl ester (AD 20);

2-(2-pyridylthio)-hexanedioic acid-1-methyl ester 6-pentyl ester (AD Z);

2-(2-pyridylthio)-decanedioic acid-10-ethyl ester 1-methyl ester (AD 32).

In yet another embodiment of the present invention, said compounds are useful as anti-inflammatory agent.

In yet another embodiment of the present invention, process for the preparation of compound of general formula 1 comprising the steps of:

i. providing barton ester of formula IV by known method;

(IV)

Wherein R=—$CH_2CH_2COOC_4H_9$, —$CH_2CH_2COOC_5H_{11}$, $(CH_2)_6COOEt$, —$CH_2CH_2COOC_6H_{11}$, —$CH(COOMe)(CH_2)_3COOC_6H_{11}$, —$CH(COOMe)(CH_2)_3COOC_3H_7$, —$CH(COOMe)(CH_2)_3COOC_5H_{11}$, —$CH(COOMe)(CH_2)7COOC_2H_5$.

ii. diluting barton ester as provided in step (i) with solvent up to 25 ml;
iii. irradiating the diluted barton ester under sun light at temperature in the range of 25 to 30° C. for period in the range of 15 to 20 minutes;
iv. optionally irradiating the diluted barton ester with olefin under sun light at temperature in the range of 25 to 30° C. for period in the range of 15 to 20 minutes;
v. removing the solvent from the irradiated solution as obtained in step (iv) under reduced pressure in the range of 30 to 50 millibar to obtain an oily crude product;
vi. purifying crude product as obtained in step (v) by preparative TLC to obtain the compound of general formula 1.

In yet another embodiment of the present invention, solvent used is selected from dry and degassed benzene or $CH_2Cl_2$.

In yet another embodiment of the present invention, olefin used is methyl acrylate.

In yet another embodiment of the present invention, electric bulb of 200 watt can be used to irradiate the solution for period in the range of 8 to 10 hrs.

In yet another embodiment of the present invention, said compound is prepared from the O-acyl derivative of N-hydroxy-2-thiopyridone prepared from mono pentyl ester derivative of butane dioic acid.

In yet another embodiment of the present invention, said compounds exhibiting inhibition of the LPS induced ICAM-1 (Intercellular cell adhesion molecule-1) expression and neutrophil adhesion on human endothelial cells with $IC_{50}$ in the range of 50±0.84 to 178±0.81 μM and 61±0.84 to 94±0.92 μM respectively.

In yet another embodiment of the present invention, compound RS—Z exhibiting reduction of the neutrophil influx in the lungs in a mice model of acute lung injury at doses of 0.1, 1.0 and 10 mg/kg body weight i.p. and attenuation of the LPS-induced lung injury in mice at doses of 0.1, 1.0 and 10 mg/kg body weight i.p.

In an embodiment of the present invention, bioactivity of the compound RS—Z is characterized by known biological assays selected from the group consisting of anti-inflammatory and cytotoxicity assays.

BRIEF DESCRIPTION OF THE DRAWINGS

FIG. 1.1 (Synthetic scheme of RS—Z (Formula 1a).
FIG. 1.2 (Synthetic scheme of RS-20).
FIG. 1.3 (Synthetic scheme of RS-21)
FIG. 1.4 (Synthetic scheme of RS-32)
FIG. 1.5 (Synthetic scheme of AD-Z, side product is RS—Z)
FIG. 1.6 (Synthetic scheme of AD-20, RS-20 is side product)
FIG. 1.7 (Synthetic scheme of AD-21, side product RS-21)
FIG. 1.8 (Synthetic scheme of AD-32, side product RS-32)
For first four compounds, preparation of Barton ester as well as its photolysis is shown and for the rest photolysis of Barton ester with methyl acrylate is shown only, its preparation is same as first four).

DETAIL DESCRIPTION OF THE INVENTION

Present invention provides anti-inflammatory Pyridin-2-yl sulfanyl acid ester compounds of general formula 1

General Formula 1 wherein
$R_1$=H;
$R_2$=H, COOMe;
$R_3$=$(CH_2)_nCOOR_4$;
$R_4$=$C_2H_5$, $C_3H_7$, $C_4H_9$, $C_5H_{11}$, $C_6H_{11}$;
n=1-7.

Chemically these compounds are classified as Pyridin-2-yl sulfanyl acid ester or Carboxylic acid, n-(2-pyridinylthio)-, alkyl ester. These types of compounds are prepared from O-acyl derivative of N-Hydroxy-2-thiopyridone (popularly called as Barton ester). The Barton ester of interest is irradiated under Sun light or under visible light for a specified period of time to get the desired product. Compounds of interest may also be prepared:
i. from Barton ester under thermal condition;
ii. from a pure isolated Barton ester through photolysis under sunlight/normal light or from the Barton ester prepared in situ without further treatment or isolation;
iii. from the photolysis reaction of Barton ester alone or in presence of some olefinic trap as detailed elsewhere.

The compounds of interest may be purified through chromatographic means and isolated from the photolysis reaction mixture of the Barton ester. The derivatives of Pyridin-2-yl sulfanyl acid esters were synthesized and characterized. These compounds were further screened for their anti-inflammatory activity with respect to inhibition of adhesion of neutrophils, isolated from human peripheral blood, onto the surface of human umbilical vein endothelial cells (HUVEC) as a result of inhibition of the cytokine-stimulated expression of ICAM-1. The $IC_{50}$ values for the compounds (Table 1) with respect to their inhibition of ICAM-1 expression and neutrophil adhesion on endothelial cells were determined. The compounds were found to be non-toxic to endothelial cells, however, the maximum tolerable dose for each compound was found to be different.

TABLE 1

Screening data of the derivatives synthesized.

| | ICAM-1 inhibition $IC_{50}$ (µM) | Neutrophil Adhesion Inhibition $IC_{50}$ (µM) | Max. tolerable dose (µM)* |
|---|---|---|---|
| RS-21 | 135 ± 0.82 | not significant | 250 |
| RS-32 | 97 ± 0.63 | 94 ± 0.92 | 500 |
| RS-20 | 79 ± 0.73 | 85 ± 0.94 | 500 |
| RS—Z | 50 ± 0.84 | 61 ± 0.84 | 500 |
| AD-21 | 117 ± 0.92 | not significant | 250 |
| AD-20 | 178 ± 0.81 | not significant | 250 |
| AD-32 | 100 ± 0.96 | not significant | 250 |
| AD—Z | 85 ± 1.52 | not significant | 250 |
| NAC (N-acetyl cysteine) (reference compound) | 6.68 mM ± 1.23 | not significant | 20 mM |

*Concentration of compounds where >95% cells are viable

The compound designated as RS—Z (Formula 1a) was found to be most potent anti inflammatory compound of the series with lowest $IC_{50}$ values for ICAM-1 and neutrophil adhesion inhibition. This compound was also found to have in-vitro maximum tolerable dose of 500 µM on human umbilical vein endothelial cell (HUVEC).

Formula 1a (RS—Z)

Characterization of the anti-inflammatory lead compound of formula 1a was carried out by known analytical methods such as infrared, mass and nuclear magnetic resonance spectroscopy and biological assays such as anti-inflammatory assay and cytotoxicity assay having following characteristics:

IR (CHCl3): ($cm^{-1}$) 3060, 2960, 2853, 1780, 1733, 1452, 1415, 1123, 1043, 987;

MS (m/z) %: 253.8 (M+1)

$^1$H NMR (CDCl$_3$): (∂ ppm) 8.50 (ddd, J=4.9, 1.8, 1 Hz, 1H), 7.48 (ddd, J=8, 7.8, 1.8 Hz, 1H), 7.17 (td, J=8, 4.5 Hz, 1H), 7.00 (ddd, J=7.8, 4.9, 1 Hz, 1H), 4.10 (t, J=7.2 Hz, 2H), 3.15 (t, J=7 Hz, 2H), 2.30 (t, J=7 Hz, 2H), 1.70-1.20 (m, 6H), 0.90 (t, J=7 Hz, 3H);

$^{13}$C NMR (CDCl$_3$): (∂ ppm) 173.00, 159.23, 148.17, 136.27, 122.30, 119.17, 60.75, 33.15, 29.10, 26.12, 22.65, 20.37, 14.75

The said compound of formula 1a causes
a) Inhibition of the LPS-induced ICAM-1 expression on human endothelial cells and has $IC_{50}$ of 50 µM.
b) Inhibition of the LPS-induced neutrophil adhesion on the surface of human endothelial cells with $IC_{50}$ of 61 µM.
c) Reduction of the neutrophil influx in the lungs in a mice model of acute lung injury at doses of 0.1, 1.0 and 10 mg/kg body weight., i.p.
d) Attenuation of the LPS-induced lung injury in mice at doses of 0.1, 1.0 and 10 mg/kg body weight., i.p.

TABLE 2

Comparison of RS—Z with known compounds in acute lung Injury model.

| Compound | Efficacious Dose (mg/kg) | Class of compound | Reference |
|---|---|---|---|
| 1. RS—Z (3-(Pyridin-2-yl sulfanyl)-propionic acid pentyl ester | 10 mg/kg | Pyridin-2-yl sulfanyl acid ester | — |
| 2. Dexamethasone | 3 mg/kg | Glucocorticoid | Clin. Hemorheol. microcirc., 2009, 41(2), 117-25 |
| 3. N-acetyl Cysteine | 150 mg/kg | Antioxidant and free-radical scavenger | Clinical and Experimental pharmacology and Physiology, 2006, January-February, 33(1-2), 33-40 |
| 4. Rolipram | 5 mg/kg | Phosphodiesterase 4 inhibitor | Am J Respir. Cell mol Biol., 1998, 18(3), 411-20 |

TABLE 2-continued

Comparison of RS—Z with known compounds in acute lung Injury model.

| Compound | Efficacious Dose (mg/kg) | Class of compound | Reference |
| --- | --- | --- | --- |
| 5. Water-soluble Vitamin E derivative(α-D-glucopyranosyl)methyl-2,5,7,8-(tetramethyl)chroman-6-ol) | 10 mg/kg | Antioxidant | Clinical and Experimental pharmacology and Physiology, 2004, 31(4), 226-230 |
| 6. Thalidomide (α-N-phthalimidoglutarimide) | 100 mg/kg | Sedative | J. Biomed. Sci., 2004, 11, 591-598 |

The derivatives of Pyridin-2-yl sulfanyl acid esters were characterized by IR, NMR and mass spectroscopy prior to screening for their anti-inflammatory activity with respect to inhibition of adhesion of neutrophils, isolated from human peripheral blood, onto the surface of human umbilical vein endothelial cells (HUVECs) as a result of inhibition of the cytokine-stimulated expression of ICAM-1.

The compounds were found to be non-toxic to endothelial cells, however, the maximum tolerable dose for each compound was found to be different. The $IC_{50\ values}$ for the compounds (Table 1) with respect to their inhibition of ICAM-1 expression and neutrophil adhesion on endothelial cells were determined.

Biological Activity of the Compound

Cell-cell interactions that are critical for normal hemostasis, immune surveillance, and vascular wall integrity are mediated by glycoproteins known as cell adhesion molecules (CAMs). These protein molecules mediate leukocyte-endothelial cell interactions that occur in all segments of the microvasculature under certain physiological (eg, hemostasis) and pathological (eg, inflammation) conditions (Muller A M et al, 2002). The bidirectional interactions between leukocytes and endothelial cells are influenced by cytokines such tumor necrosis factor (TNF-α), IL-1β and gram-negative bacterial polysaccharide (LPS) that drastically increase the expression of cell adhesion molecules on the surface of the endothelium (Sato N et al, 2000). Aberrant interaction between the leukocyte and the endothelial cell (EC) results in the uncontrolled inflammation leading to various inflammatory disorders. One of the promising therapeutic target to control the dysregulated leukocyte-endothelial interaction would be to modulate the cytokine-induced expression of cell molecules (Bhatia M, 1998). In order to treat the deleterious inflammatory responses in human diseases, anti-inflammatory agents are extensively used clinically. However, anti-inflammatory drugs such as NSAIDs (Non-steroidal anti-inflammatory drugs), corticosteroids and chemotherapeutic agents have severe side effects. Therefore, there is an unmet therapeutic need to develop more selective and safe drugs to treat inflammatory disorders.

In search of a new anti-inflammatory drug with negligible side effects, the novel synthesized compounds were screened for their anti-inflammatory activity with respect to inhibition of adhesion of neutrophils isolated from human peripheral blood, onto the surface of human umbilical vein endothelial cells (HUVECs) as a result of inhibition of the cytokine-stimulated expression of ICAM-1.

The present invention showed that the compounds are not toxic to endothelial cells, however, the maximum tolerable dose for each compound is different. The $IC_{50}$ values for the compounds (Table 1) with respect to their inhibition of ICAM-1 expression and neutrophil adhesion on endothelial cells were calculated. RS—Z (formula 1a) showed the lowest $IC_{50}$ values of 50 µM for ICAM-1 inhibition and 61 µM for neutrophil adhesion inhibition.

Therefore, the present invention showed that the most active compound of the series was 3-(Pyridin-2-yl sulfanyl)-propionic acid pentyl ester (RS—Z, formula 1a) that could inhibit both the expression of cell adhesion molecule ICAM-1 (intercellular adhesion molecule-1) ($IC_{50}$=50 µM) and the neutrophil adhesion onto the surface of human endothelial cells ($IC_{50}$=61 µM).

Figure 1:
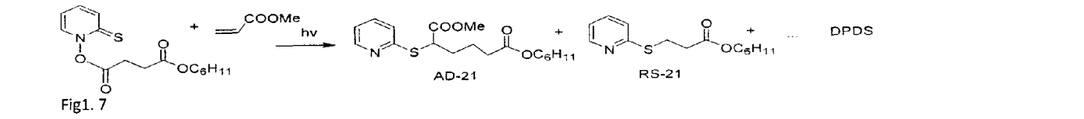
FIG. 1. Represent scheme for the preparation of compound of general formula 1.
Figure 2A:
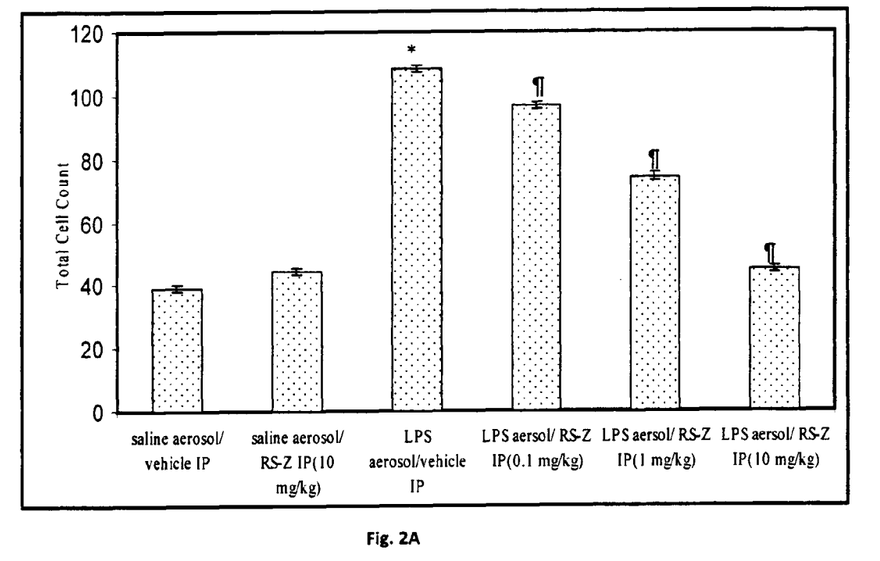
FIG. 2A. Total cell counts in the BALF (bronchoalveolar lavage fluid) supernatant in mice. Post-treatment with IP (intraperitoneal) administration of RS—Z dose-dependently reduced the increased cell counts induced by LPS. The data are mean±S.E.M. of six mice for each group.* P<0.001 vs. Saline aerosol/vehicle IP; P<0.001 vs. LPS aerosol/vehicle IP.
Figure 2B:
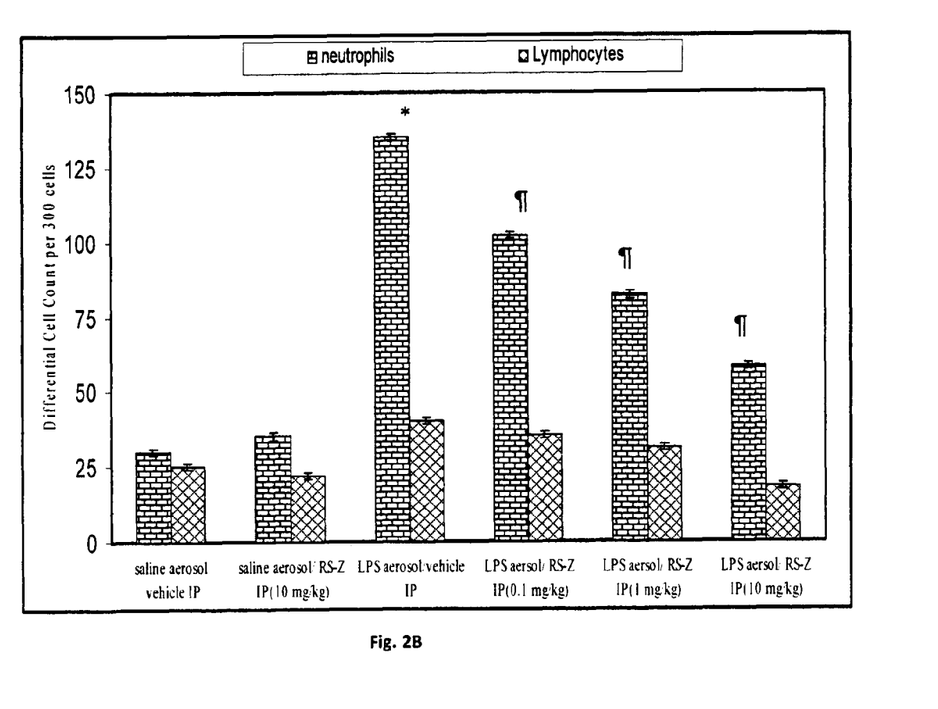
FIG. 2B. Differential cell count in the BALF supernatant in mice. Post-treatment with RS—Z dose-dependently reduced the increased neutrophil count induced by LPS. The data are mean±S.E.M. of six mice for each group. *P<0.001 vs. Saline aerosol/vehicle IP; P<0.001 vs. LPS aerosol/vehicle IP.
Figure 3:
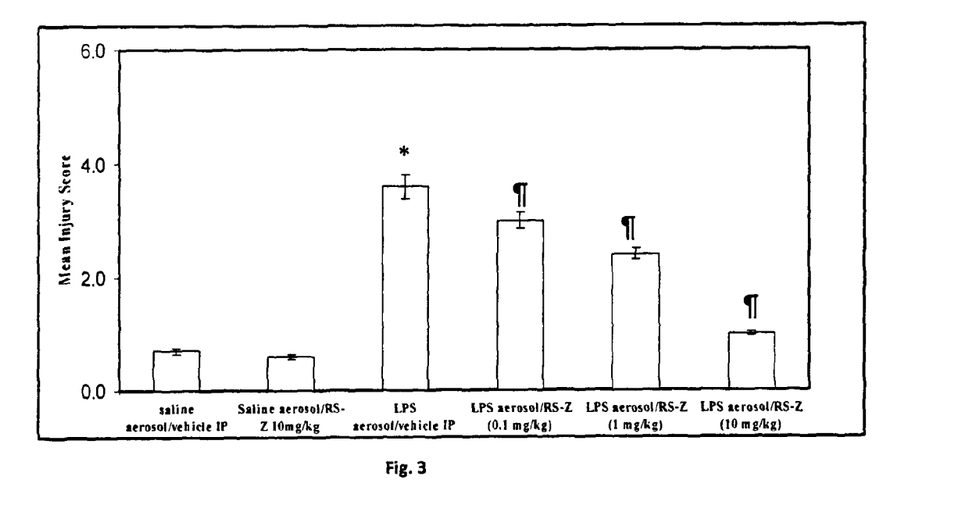
FIG. 3: Effects of RS—Z on the injury score in the lung tissue in mice of acute lung injury induced by lipopolysaccharide (LPS) aerosol inhalation. Post treatment with RS—Z dose-dependently reduced the increased injury induced by LPS. The data are mean±S.E.M. of six mice for each group. * P<0.0001 vs. Saline aerosol/vehicle IP; P<0.0001 vs. LPS aerosol/vehicle IP.
Figure 11:
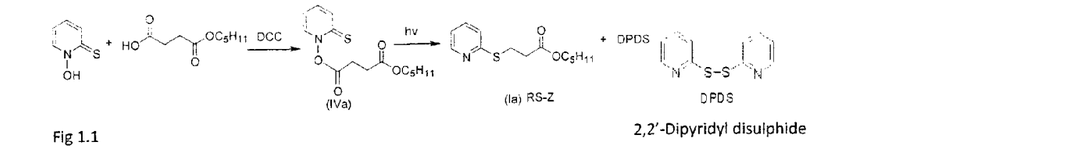
Figure 12:
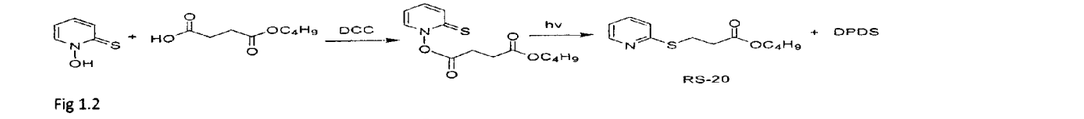
Figure 13:
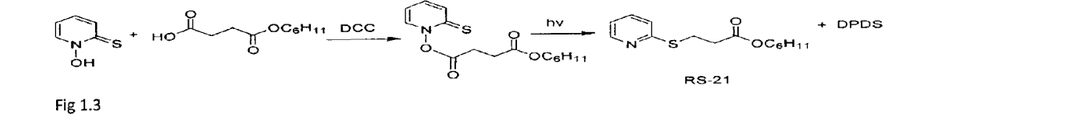
Figure 14:
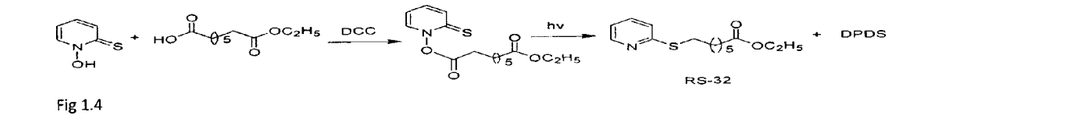
Figure 15:
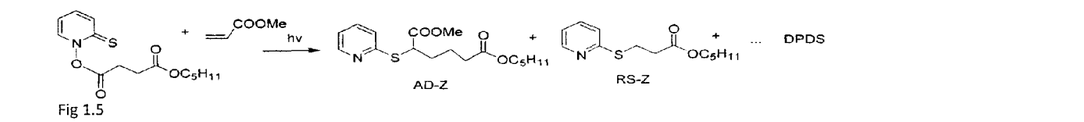
Figure 16:
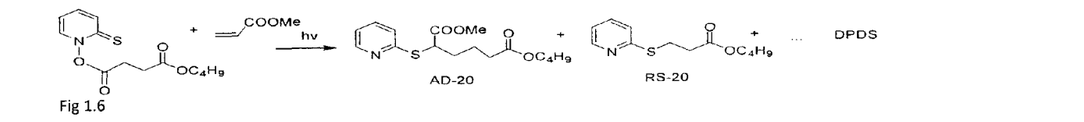

The compound RS—Z was tested for in-vivo efficacy in a mice model. Mice were sensitized with aerosol inhalation of LPS to develop the characteristic features of acute lung injury such as massive infiltration of neutrophils into the lung leading to alveolar damage. These features were characterized by determining the lung injury score using the known scoring methods from the H & E (hematoxylin & eosin) stained slides of the excised lung tissue, total and differential cell count was performed in the BALF (bronchoalveolar lavage fluid) to determine the infiltration status.

The present invention showed that the novel compound RS—Z could significantly alleviate pulmonary neutrophil infiltration in mice model of acute lung injury induced by bacterial polysaccharide at a dose of 10 mg/kg body weight administered intraperitoneally. The present invention showed that RS—Z significantly reduced the lung injury caused by bacterial polysaccharide challenge at a dose of 10 mg/kg body weight.

EXAMPLES

Following examples are given by way of illustration therefore should not be construed to limit the scope of the present invention.

Example 1

Step 1

Preparation of Butane Dioic Acid Mono Alkyl Ester (II)

3 mmol (300 mg) of succinic anhydride was dissolved in 5 ml of dichloroethane in a 50 ml conical flask. To the solution was added 3 mmol of an alkanol followed by 151 mg (1.5 mmol) of dry triethylamine. The flask was loosely stoppered with cotton plug and irradiated in a microwave oven at 80% power (480 watt) for 3 minutes. The reaction mixture was cooled and diluted with 15 ml of ethyl acetate. The ethyl acetate extract was washed 3 times with 30 ml of water each. The organic layer was dried over anhydrous sodium sulfate and evaporated under reduced pressure. The crude product was purified by preparative TLC using 1:4 (ethyl acetate: hexane) solvent system to get around 75% of pure butanedioic acid mono alkyl ester (II) as gum. The product was characterized in a usual way by recording IR, NMR and MS spectra.

(II)

R may be alkyl group like methyl, ethyl, propyl, butyl, pentyl, hexyl etc or substituted alkyl group, cycloalkyl, benzyl, naphthyl etc.

Step 2

Preparation of Alkane Dioic Acid Mono Alkyl Ester (III)

(III)

Alkane dioic acid mono alkyl ester was prepared from alkane dioic acid through steps (a) and (b) as discussed below:

(a) Preparation of the Diester

To a solution of 3 mmol of the alkane dioic acid in 5 ml of absolute alkanol in a 50 ml conical flask was added two drops of conc. $H_2SO_4$ acid. The flask was loosely stoppered with a cotton plug and irradiated in a microwave oven at power 60% (360 watt) for four minutes. The reaction mixture was cooled and diluted with 15 ml of ethyl acetate. The ethyl acetate layer was washed with aqueous sodium bicarbonate solution to remove the unreacted diacid. The ethyl acetate layer was finally washed with water and dried over anhydrous sodium sulfate. The solvent was removed by distillation under reduced pressure in a rotary evaporator to get 75% of the diester as oil. The structure of the alkane dioic acid diester was confirmed by recording IR, NMR and MS spectra.

(b) Selective Hydrolysis of the Dioic Acid Dialkyl Ester to Mono Ester (III)

To a three necked 250 ml R.B. flask fitted with mercury sealed mechanical stirrer, a dropping funnel and a reflux condenser with a $CaCl_2$ guard tube on its top was added 0.01 mol of the dialkyl ester of alkane dioic acid in 10 ml absolute ethanol with continuous stirring at room temperature. A solution of 0.01 mol (560 mg) of potassium hydroxide in 10 ml absolute ethanol was added drop wise over a period of one hour under stirring condition. During addition of alkali, white crystalline precipitate was observed to form. After complete addition of potassium hydroxide, stirring was continued for further two hours and the reaction mixture was kept overnight at RT. Excess alcohol was distilled off under reduced pressure, the residue was diluted with water (10 ml) and the aqueous layer was extracted with ether (3×10 ml) to remove the unchanged diester from potassium salt. The potassium salt in the aqueous layer was cooled to 3° C., and acidified by adding 4 ml of 6N HCl drop wise over a period of 30 minutes. The aqueous layer was extracted with 3×10 ml of ether and then the ether layer was dried over anhydrous $Na_2SO_4$. Excess ether was evaporated on a water bath. The crude residue was purified by column chromatography to obtain about 48% of pure acid ester (III) as gum. The acid ester (III) was characterized as usual way.

Example 2

Preparation of Butanedioic Acid n-Pentyl Monoester (IIa)

Butanedioic acid n-pentyl monoester (IIa) was prepared by following the same procedure as described for the preparation of (II) (step 1). Amounts of substrate and reagents used in the reaction are mentioned below. Product (IIa) was isolated as gum after purification by using column chromatography.

Succinic anhydride: 300 mg=3 mmol
n-petanol: 264 mg=3 mmol
Dry triethylamine: 151 mg=1.5 mmol
Dichloroethane: 5 ml
MW power: 70% (480 watt)
Time: 3 minutes (IIa)

Product (IIa) was characterized as follows:

1H NMR (CDCl$_3$): (δ ppm) 10.10 (brs, 1H), 4.20 (t, J=7.2 Hz, 2H), 2.60 (t, J=7 Hz, 4H), 1.30-1.60 (overlapping multiplet, 6H) and 0.93 (m, 3H).

IR (CHCl$_3$): (cm$^{-1}$) 340, 2980, 1730, 1710, 1460, 1342, 1220, 1180, 1120, 1029.

MS (m/z) %: 187 (M+1)

Example 3

Preparation of Intermediate

Preparation of Butane Dioic Acid Butyl Monoester (IIb)

Butane diooic acid butyl monoester (IIb) was prepared following the procedure described for preparation of (II). (Step 1) Amounts of substrate and reagents used in the reaction are as mentioned bellow. The crude product was purified by using column chromatography.

Succinic anhydride: 300 mg=3 mmol
n-butanol: 222 mg=3 mmol
Dry triethylamine (TEA): 151 mg=1.5 mmol
Dichloromethane: 3 ml
MW power: 80% (480) watt
Time: 3 minutes
Yield: 365 mg=70%

(IIb)

(IIIa)

Product (IIb) was characterized as follows:
$^1$H NMR (CDCl$_3$): (δ ppm) 10.20 (s, H), 4.20 (t, J=7 Hz, 2H), 2.60 (m, 4H), 1.60-1.30 (m, 4H), 0.92 (t, J=7 Hz, 3H).
IR (CHCl$_3$): (cm$^{-1}$) 3455, 2981, 2942, 1733, 1710, 1462, 1447, 1375, 1349, 1220, 1147, 1077, 1029.
MS (m/z) %: 173 (M+1)

Example 4

Preparation of Intermediate

Preparation of Octane Dioic Acid Mono Ethyl Ester

Octane dioic acid monoethyl ester was prepared from octane dioic acid through steps (a) and (b) as discussed in Example 1, Step 2 above.

(a) Preparation of Octane Dioic Acid Diethyl Ester

Octane dioic acid diethyl ester was prepared by following the procedure described for the preparation of diester in example 2 (a). The diester was isolated as gum in 70% yield. The amounts of substrate and reagents used in the reaction are mentioned below.
Octane dioic acid: 522 mg=3 mmol
Absolute ethanol: 5 ml
Conc. H$_2$SO$_4$ acid: 2 drops
MW power: 60%
Time: 3 minutes
Yield: 483 mg=70%

Octane Dioic Acid Diethyl Ester

The diester was characterized as follows.
$^1$H NMR (CDCl$_3$): (δ ppm) 4.10 (q, J=7 Hz, 4H), 2.50 (t, J=7 Hz, 4H), 1.50-1.60 (m, 4H), 1.30-1.10 (m, 10H).
IR (CHCl$_3$): (cm$^{-1}$) 2980, 2945, 2870, 1712, 1451, 1412, 1220, 1157, 1020, 928, 770.
MS (m/z) %: 231 (M+1).

(b) Selective Hydrolysis of Diethyl Ester of Octane Dioic Acid to Get Octane Dioic Acid Mono Ethyl Ester (IIIa)

Selective hydrolysis of diethyl ester of octane dioic acid to get acid ester (IIIa) was done by following the procedure described for the selective hydrolysis of ester in example 2 (b). The product (IIIa) was isolated as gum in 49% yield after purification by column chromatography.

The acid ester (IIIa) was characterized as follows.
$^1$H NMR (CDCl$_3$): (δ ppm) 9.30 (br, s, H), 4.10 (q, J=6 Hz, 2H), 2.30-2.50 (m, 4H), 1.60 (m, 4H), 1.30-1.10 (overlapping multiplet, 7H).
IR (CHCl3): (cm$^{-1}$) 3022, 2970, 2942, 2882, 1730, 1717, 1460, 1380, 1217, 1180, 1060, 940.
MS (m/z) %: 203 (M+1).

Example 5

Preparation of Intermediate

Preparation of Pentanedioic Acid Monopropyl Ester (IIIb)

Pentane dioic acid mono propyl ester was prepared from pentane dioic acid through two steps as described below.

(a) Preparation of Pentane Dioic Acid Dipropyl Ester

To a solution of 396 mg (3 mmol) of pentane dioic acid in 3 ml of n-propanol in a 50 ml conical flask was added 2 drops of conc. H$_2$SO$_4$ acid. The flask was loosely stoppered by cotton and subjected to irradiation in a microwave oven at power 60% (360 watt) for 4 minutes. The reaction mixture was cooled and diluted with 15 ml ethyl acetate. The ethyl acetate extract was washed with aq. sodium bicarbonate solution to remove the unreacted diacid. The ethyl acetate layer was finally washed with water and dried over anhydrous sodium sulfate. The solvent was removed by distillation under reduced pressure in rotary evaporator. The oily crude so obtained was purified by using column chromatography. The diester was recovered as gum in 70% yield.

Pentane Dioic Acid Dipropyl Ester

The diester was characterized as follows:
$^1$H NMR (CDCl$_3$): (δ ppm) 4.15 (t, J=7 Hz, 4H), 2.60 (t, J=7 Hz, 4H), 1.60 (t, J=7 Hz, 4H), 1.15 (m, J=7 Hz, 4H), 0.90 (t, J=7 Hz, 6H).
IR (CHCl$_3$): (cm$^{-1}$) 2960, 2910, 2830, 1730, 1448, 1370, 1352, 1265, 1210, 1160, 1030.
ms (m/z) %: 202 (M+1).

(b) Selective Hydrolysis of Pentanedioic Acid Dipropyl Ester

To a doubled necked 250 ml Round Bottom (R.B.) flask fitted with a dropping funnel and a reflux condenser with a CaCl$_2$ guard tube on its top was added 0.010 mol of the dipropyl ester of the pentanedioic acid in 10 ml of absolute ethanol at room temperature. A solution of 560 mg (0.01 mmol) of potassium hydroxide in 10 ml of absolute ethanol was added drop wise over a period of one hour under continuous stirring. During addition of the alkali, white crystalline precipitate was observed to form. After complete addition of potassium hydroxide, stirring was continued for another two hours and the reaction mixture was kept overnight at room temperature. Excess alcohol was distilled off under reduced pressure, the residue was diluted with water (10 ml) and the aqueous layer was extracted with ether (3×10 ml) to remove the unchanged ester from potassium salt. The potassium salt in the aqueous layer was then cooled to 5° C., and acidified by adding 4 ml of 6N HCl acid drop wise over a period of 30 minutes. The aqueous layer was extracted with 3×10 ml of ethyl acetate and the ethyl acetate layer was dried over anhydrous $Na_2SO_4$. Excess ethyl acetate was evaporated under reduced pressure in rotary evaporator. The oily crude was purified by column chromatography to obtain 49% of pure acid ester (15b) as gum.

(IIIb)

The acid ester (IIIb) was characterized as follows:
$^1$H NMR (CDCl$_3$): (δ ppm) 10.30 (br, s, H), 4.20 (t, J=7 Hz, 2H), 2.50 (t, J=7 Hz, 4H), 1.60 (m, 2H), 1.20 (m, 2H), 0.90 (t, J=7 Hz, 3H).
IR (CHCl$_3$): (cm$^{-1}$) 3420, 2960, 2940, 1732, 1718, 1420, 1395, 1215, 1185, 1062, 945.
MS (m/z) %: 180 (M+1).

Example 6

Preparation of Intermediate

Preparation of Hexane Dioic Acid Mono Ethyl Ester (IIIc)

Hexane dioic acid monoethyl ester was prepared from hexane dioic acid through steps (a) and (b) discussed above in example 1, step 2 for the preparation of (III).

(a) Preparation of Diethyl Ester of Hexane Dioic Acid

Diethyl ester of hexane dioic acid was prepared by following the same procedure as described for the preparation of the diester in Example 2 (a). Compound was isolated as oil in 75% yield after purification by column chromatography. Amounts of substrate and reagents used in the reaction are as mentioned below.
Hexane dioic acid: 439 mg=3 mmol
Absolute ethanol: 5 ml
Conc. $H_2SO_4$ acid: 2 drops
M.W. power: 80%
Time: 3 minutes Ethyl Diester of Hexanedioic Acid The diester was characterized as follows.
Yield: 75%
$^1$H NMR (CDCl$_3$): (δ ppm) 4.15 (q, J=7 Hz, 4H), 2.60 (t, J=7 Hz, 4H), 1.60 (m, 4H), 1.10 (t, J=5 Hz, 6H).
IR (CHCl$_3$): (Cm$^{-1}$) 2980, 2939, 2612, 1730, 1458, 1373, 1349, 1265, 1214, 1162, 1033.
MS (m/z) %: 203 (M+1)

(B) Selective Hydrolysis of Diethyl Ester of Hexane Dioic Acid to Get Hexane Dioic Acid Mono Ethyl Ester (IIIc)

Selective hydrolysis of diethyl ester to get acid ester (IIIc) was done by following the procedure described for the selective hydrolysis of diethyl ester in example 2 (b). The product (IIIc) was isolated as oil in 52% yield after purification by column chromatography.

(IIIc)

The acid ester (IIIc) was characterized as follows.
$^1$H NMR (CDCl$_3$): (δ ppm) 9.60 (br, s, H), 4.10 (q, J=3 Hz, 2H), 2.60 (t, J=7 Hz, 4H), 1.60 (m, 4H) and 1.00 (t, J=7 Hz, 3H).
IR (CHCl$_3$): (cm$^{-1}$) 3024, 2980, 2939, 2882, 1730, 1717, 1414, 1396, 1362, 1217, 1173, 1060, 940, 759, 668.
ms (m/z) %: 174 (M+1).

Example 7

Preparation of Intermediate

Preparation of O-Acyl Derivative of N-Hydroxy-2-thiopyridone (Barton Ester) (IV)

(IV)

Ester or more strictly the anhydride derivative of N-Hydroxy-2-thiopyridone with carboxylic acids (O-acyl derivative) is popularly called as Barton Ester. Barton Esters can be prepared by either acid chloride method or by direct coupling method of acid with N-Hydroxy-2-thiopyridone in presence of dicyclohexyl carbodiimide (DCC). As Barton Esters are sensitive to heat, light and moisture at normal conditions, they are always prepared under cover of aluminum foil in a dry and inert atmosphere immediately before their use and in most cases Barton Esters are neither isolated nor characterized.

DCC Method:

A double necked round bottom flask fitted with an inert gas inlet and a stopper, was covered with a sheet of aluminum foil. A solution of 1 mmol of the acid in 25 ml of dry solvent (Benzene, dichloromethane, Toluene etc.) was placed in the R.B. To the stirred solution, 0.99 mmol (125 mg) of N-hydroxy-2-thiopyridone was added, followed by 0.99 mmol of DCC at the same temperature. Progress of the reaction was monitored by TLC. The reaction mixture was quickly filtered by passing through a bed of silica gel to separate the precipitate of DCC-urea and the filtrate (Barton Ester) was used for the next reaction without further isolation.

Acid Chloride Method:

A solution of 1 mmol of N-hydroxy-2-thiopyridone in 20 ml dry benzene or dichloromethane was placed in a double necked R.B. covered with an aluminium foil under inert atmosphere. A solution of 0.99 mmol of the acid chloride in 20 ml of dry benzene or dichloromethane was added very slowly with stirring followed by 0.1 ml of dry pyridine at 5-10° C. Stirring was continued till the completion of the reaction. Reaction was monitored by TLC (2:1 hexane:ethyl acetate). A single yellow spot on the TLC plate confirmed the completion of the reaction. Barton Ester so obtained was utilized in the next step without any purification and characterization.

General Procedure for the Preparation of Acid Chloride

Carboxylic acid chlorides were prepared immediately prior to their use by either of the methods mentioned below and used in the next reaction without isolation and characterization. (a) Thionyl chloride method (b) Phosphorous trichloride method (c) Oxalyl chloride method.

Example 8

Preparation of Intermediate

Preparation of O-acyl Derivative of N-Hydroxy-2-thiopyridone (Barton Ester) (IVa) with Butane Dioic Acid n-pentyl Monoester (IIa)

Succinic acid pentyl ester-2-thiopyridine-1-yl ester

The required ester was prepared by DCC method as described before in example 7 for the preparation of the compound type (IV).

Butane dioic acid mono pentyl ester: 188 mg=1 mmol.
N-hydroxy-2-thiopyridone: 125 mg=0.99 mmol.
1,3-dicyclohexylcarbodiimide (DCC): 204 mg=0.99 mmol.
Dry benzene: 20 ml
Time: 2.10 hrs
Temperature: 20° C. (room temp.)
Yield: 100% on TLC Example 9

Preparation of Intermediate

Preparation of O-acyl Derivative of N-Hydroxy-2-thiopyridone (Barton Ester) (IVb) with Octane Dioic Acid Mono Ethyl Ester (IIIa)

Octane Dioic Acid Ethyl Ester-2-thiopyridine-1-yl Ester

The required ester was prepared by DCC method as described before in example 8 for the preparation of the compound type (IV).

Octane dioic acid ethyl monoester: 202 mg=1 mmol
N-hydroxy-2-thiopyridine: 125 mg=0.99 mmol
1,3-dicyclohexyl carbodiimide (DCC): 204 mg=0.99 mmol.
Dry benzene: 20 ml
Time: 2 hrs 30 min.
Temperature: 25° C. (room temp.)
Yield: 100% (on TLC)

Example 10

General Procedure for the Photolysis of N-Hydroxy-2-thiopyridone Ester (Barton Ester) (IV) Blank Photolysis to Get Compound of Type (I)

The O-acyl derivatives of N-hydroxy-2-thiopyridone (Barton ester) (IV) were prepared in situ either by following acid chloride method or by DCC method as above. After removing the DCC-urea by filtration, the filtrate containing crude Barton Ester (1-0.9 mmol) was placed in a 100 ml round bottom flask and diluted with dry and degassed benzene or $CH_2Cl_2$ up to 25 ml. The ester solution was irradiated under sun light at temperature in the range of 15 to 30° C. Irradiation of the Barton ester under a normal 200 watt bulb kept at a distance 30 cm from the reaction flask also gave almost same result. Under the sun light the reaction requires 15 to 20 minutes for completion of photolysis whereas time required for photolysis under electric bulb of 200 watts is in the range of 8-10 hrs. The progress of the reaction was monitored by TLC (1:2 EA:hexane). Disappearance of the characteristic yellow colour of the reaction mixture as well as the yellow spot on the TLC indicated the completion of the photolysis reaction. On completion, the solvent of the reaction mixture was distilled off under reduced pressure in the range of 30 to 50 millibar to obtain an oily crude product in general. Purification by preparative TLC gave the photolysis products in different amount of yields. All the products were identified by spectroscopic analysis such as IR, NMR and MS. Blank photolysis of compound in structure (IV) is a rearrangement reaction as shown below.

Example 11

Preparation of Product RS—Z

Blank Photolysis of Succinic Acid Pentyl ester-2-thiopyridine-1-yl Ester (IVA)

Photolysis of the Barton ester (IVa) i.e. Succinic acid pentyl ester-2-thiopyridine-1-yl ester under sun light as per the procedure stated in example 10 above was done.

Butane dioic acid pentyl monoester: =188 mg=1 mmol
N-hydroxy-2-thiopyridone: =124 mg=0.99 mmol
1,3,-Dicyclohexyl carbodiimide: =204 mg=0.99 mmol
Dry dichloromethane: =25 ml
Yield of Barton ester: =100% (on TLC)
Time for photolysis: =20 min
Temperature: =25° C. (room temp.)

After completion of photolysis, solvent was removed under reduced pressure and the oily crude was purified by preparative TLC (1:5 EA:Hexane). The pure products so obtained were characterized as follows:

3-(2-pyridylthio)propionic acid pentyl ester

Yield: 172 mg (68%)

$^1$H NMR (CDCl$_3$): (∂ ppm) 8.50 (ddd, J=4.9, 1.8, 1 Hz, 1H), 7.48 (ddd, J=8, 7.8, 1.8 Hz, 1H), 7.17 (td, J=8, 4.5 Hz, 1H), 7.00 (ddd, J=7.8, 4.9, 1 Hz, 1H), 4.10 (t, J=7.2 Hz, 2H), 3.15 (t, J=7 Hz, 2H), 2.30 (t, J=7 Hz, 2H), 1.70-1.20 (m, 6H), 0.90 (t, J=7 Hz, 3H)

IR (CHCl3): (cm$^{-1}$) 3060, 2960, 2853, 1780, 1733, 1452, 1415, 1123, 1043, 987.

$^{13}$C NMR (CDCl$_3$): (∂ ppm) 173.00, 159.23, 148.17, 136.27, 122.30, 119.17, 60.75, 33.15, 29.10, 26.12, 22.65, 20.37, 14.75

MS (m/z) %: 253.8 (M+1)

Example 12

Preparation of Product RS-32

Blank Photolysis of Octane Dioic Acid Ethyl ester-2-thiopyridine-1-yl Ester (IVb)

Photolysis of the Barton ester (IVb) i.e. Octane dioic acid ethyl ester-2-thiopyridine-1-yl ester under sun light as per the procedure stated in example 11 above was done.

n = 4

Octane dioic acid ethyl monoester: =202 mg=1 mmol

N-hydroxy-2-thiopyridone: =124 mg=0.99 mmol 1,3,-Dicyclohexyl carbodiimide: =204 mg=0.99 mmol

Dry dichloromethane: =25 ml

Yield of Barton ester: =100% (on TLC)

Time for photolysis: =18 min

Temperature: =20° C. (room temp.)

After completion of photolysis, solvent was removed under reduced pressure and the oily crude was purified by preparative TLC (1:5 EtAc:Hexane). The pure products so obtained were characterized as follows:

n = 4, Et = C$_2$H$_5$ 7-(2-pyridylthio)heptanoic acid ethyl ester

Yield: 191 mg (68%)

$^1$H NMR (CDCl$_3$): (∂ ppm) 8.39 (ddd, J=4.9, 1.8, 1 Hz, 1H), 7.40 (ddd, J=8, 7.8, 1.8 Hz, 1H), 7.16 (td, J=8, 4.5 Hz, 1H), 6.99 (ddd, J=7.8, 4.9, 1 Hz, 1H), 4.10 (q, J=7 Hz, 2H), 3.15 (t, J=7 Hz, 2H), 2.40 (t, J=7 Hz, 2H), 1.70-1.30 (m, 8H), 1.10 (t, J=7 Hz, 3H)

IR (CHCl$_3$): (cm$^{-1}$) 3050, 2950, 2870, 1730, 1580, 1462, 1416, 1280, 1225, 1040.

$^{13}$C NMR (CDCl$_3$): (∂ ppm) 173.05, 157.25, 149.60, 136.42, 122.27, 119.25, 80.50, 35.82, 33.25, 31.16, 30.70, 28.65, 25.32, 14.60.

MS (m/z) %: 267.8 (M+1)

Example 13

Preparation of Product AD-Series

General Procedure for Photolysis of Barton Esters (IV) in Presence of Olefin as Trap O-acyl derivative of N-hydroxy-2-thiopyridone (Barton Esters, 1 mmol), prepared in situ or isolated as pure was placed in a 100 ml size round bottomed flask covered by aluminum foil. The ester solution was diluted up to 23 ml by adding anhydrous and digassed benzene or CH$_2$Cl$_2$. In an inert atmosphere, 5 mmol of an olefin like methyl acrylate was added to the solution and irradiated with sunlight at room temperature of 27° C. Irradiation with light from 200 W bulb kept a distance of 30 cum from the reaction served the same purpose giving almost the same result except slight decrease in yield. As discussed earlier, photolysis under 200 W light requires much more time (8-10 hrs) as compared to photolysis under sunlight (15 to 20 minutes). The progress of the reaction was monitored by TLC. Disappearance of the characteristic yellow spot of Barton ester on TLC plate indicated the completion of the reaction. The solvent was removed under reduced pressure to obtain an oily crude product in general. Purification by chromatographic means gave the photolytic products in different amount of yields. All the products were characterized by spectroscopic analysis such as IR, NMR and MS.

Example 14

Preparation of Product AD-Z

Photolysis of Barton Esters (IVa) in Presence of Olefin as Trap

Photolysis of the Barton ester (IVa) i.e. Succinic acid pentyl ester-2-thiopyridine-1-yl ester in presence of methyl acrylate under sun light as per the procedure stated in example 13 above was done.

Butane dioic acid mono pentyl ester: 188 mg=1 mmol.
N-hydroxy-2-thiopyridone: 125 mg=0.99 mmol.
1,3-dicyclohexylcarbodiimide (DCC): 204 mg=0.99 mmol.
Dry benzene: 20 ml
Time: 2.10 hrs
Temperature: 15-20° C. (room temp.).
Yield: 100% on TLC
Methylacrylate: 0.45 ml (5 mmol)
Time of photolysis: 18 min.
Yield of adduct: 170 mg (50%)

Example 15

Preparation of Product AD-32

Photolysis of Barton Esters (IVb) in Presence of Olefin as Trap

Photolysis of the Barton ester (IVb) i.e. Octane dioic acid ethyl ester-2-thiopyridine-1-yl ester in presence of methyl acrylate under sun light as per the procedure stated in example 14 above was done.

n = 4
Et = $C_2H_5$

Octane dioic acid ethyl monoester: =202 mg=1 mmol
N-hydroxy-2-thiopyridone: =124 mg=0.99 mmol
1,3,-Dicyclohexyl carbodiimide: =204 mg=0.99 mmol
Dry dichloromethane: =25 ml
Yield of Barton ester: =100% (on TLC)
Methylacrylate: =0.45 ml (5 mmol)
Time of photolysis: =18 min.
Temperature: =15-20° C. (room temp.)
Yield of adduct: =187 mg (53%)

Example 16

Cell Culture:

Primary endothelial cells were isolated from human umbilical cord using mild trypsinization (Kumar, S., Arya, P., Mukherjee, C., Singh, B. K., Singh, N., Parmar, V. S., Prasad, A. K., Ghosh, B. Novel Aromatic Ester from Piper longum and Its Analogues Inhibit Expression of Cell Adhesion Molecules on Endothelial Cells. Biochemistry. 2005, 44, 15944-15952). The cells were grown in M199 medium (Sigma, USA) supplemented with 15% heat inactivated fetal calf serum (Biological Industries, Israel), 2 mM L-glutamine (Sigma, USA), 100 units/ml penicillin (Sigma, USA), 100 μg/ml streptomycin (Sigma, USA), 0.25 μg/ml amphotericin B (Sigma, USA), endothelial cell growth factor (50 μg/ml) (Sigma, USA). At confluence, the cells were subcultured using 0.05% trypsin-0.01 M EDTA solution and were used between passages three to four.

Example 17

Cell Viability Assay

The cytotoxicity of these compounds was analyzed by colorimetric MTT (methylthiazolydiphenyl-tetrazolium bromide, Sigma, USA) assay as described (Kumar S et al, 2005). Briefly, endothelial cells were treated with DMSO alone (0.25%, as vehicle) or with different concentrations of compounds for 24 hrs. Four hrs before the end of incubation, medium was removed and 100 μl MTT (5 mg/ml in serum free medium) was added to each well. The MTT was removed after 4 hrs, cells were washed out with PBS (phosphate buffered saline, pH 7.4), and 100 μl DMSO was added to each well to dissolve water insoluble MTT-formazan crystals.

Absorbance was recorded at 570 nm in an ELISA reader (Bio-Rad, Model 680, USA). All experiments were performed at least 3 times in triplicate wells.

Example 18

Cell-ELISA for Measurement of ICAM-1

Cell-ELISA was used for measuring the expression of ICAM-1 on surface of endothelial cells (Kumar S et al, 2005) Endothelial cells were incubated with or without the test compounds at desired concentrations for the required period, followed by treatment with LPS (1 μg/ml) (BD, USA) for 16 hrs for ICAM-1 expression. The cells were fixed with 1.0% glutaraldehyde (Sigma, USA). Non-specific binding of antibody was blocked by using skimmed milk (3.0% in PBS). Cells were incubated overnight at 4° C. with anti-ICAM-1 mAb (BD, USA), diluted in blocking buffer, the cells were further washed with PBS and incubated with peroxidase-conjugated goat anti-mouse secondary antibody (Sigma, USA). After washings, cells were exposed to the peroxidase substrate (o-phenylenediamine dihydrochloride 40 mg/100 ml in citrate phosphate buffer, pH 4.5). Reaction was stopped by the addition of 2 N sulfuric acid and absorbance at 490 nm was measured using microplate reader (Spectramax 190, Molecular Devices, USA).

Example 19

Neutrophil Isolation

Neutrophils were isolated from peripheral blood of healthy individuals (Kumar S et al, 2005). Blood was collected in heparin solution (20 U/ml) and erythrocytes were removed by sedimentation against 6% dextran solution. Plasma, rich in white blood cells, was layered over Ficoll-Hypaque solution (Sigma, USA), followed by centrifugation (300 g for 20 min, 20° C.). The top saline layer and the Ficoll-Hypaque layer were aspirated leaving neutrophils/RBC pellet. The residual red blood cells were removed by hypotonic lysis. Isolated cells were washed with PBS and resuspended in PBS containing 5 mM glucose, 1 mM $CaCl_2$, and 1 mM $MgCl_2$ at a final concentration of $6 \times 10^5$ cells/ml.

Example 20

Cell Adhesion Assay

Neutrophil adhesion assay was performed under static conditions as described previously (Kumar S et al, 2005). Briefly, endothelial cells plated in 96-well culture plates were incubated with or without RS—Z at desired concentrations for 2 hrs, followed by induction with LPS (1 μg/ml) for 6 hrs. Endothelial monolayers were washed with PBS and neutrophils ($6 \times 10^4$/well) were added over it and were allowed to adhere for 1 hr at 37° C. The non-adherent neutrophils were washed with PBS and neutrophils bound to endothelial cells were assayed by adding a substrate solution consisting of o-phenylenediamine dihydrochloride (40 mg/100 ml in citrate phosphate buffer, pH 4.5), 0.1% cetrimethyl ammonium bromide, and 3-amino-1,2,4 triazole (1 mM). The absorbance was read at 490 nm using an automated microplate reader (Model 680, Bio-Rad, USA).

Example 21

Animal Challenge

BALB/c male mice 10 weeks old were randomly divided into 5 groups with 6 mice in each group.

Group 1: saline challenged/vehicle (0.25% CMC) treated
Group 2: LPS challenged/vehicle treated
Group 3: LPS challenged/RS—Z (0.1 mg/kg in 0.25% CMC) treated
Group 4: LPS challenged/RS—Z (1 mg/kg in 0.25% CMC) treated
Group 5: LPS challenged/RS—Z (10 mg/kg in 0.25% CMC) treated Mice in Groups 2, 3, 4 and 5 were challenged with an aerosol of LPS (*E. coli* strain 026:B6) at a concentration of 300 μg/ml in normal saline for 30 minutes. Mice were placed in a Plexiglas chamber ($20 \times 20 \times 10$ cm$^3$) and exposed to an aerosol generated from a nebulizer (Omtron model, USA) with an airflow rate of 9 L/min. Group 1(Control) mice were challenged with saline alone.

Example 22

Treatment of RS—Z

Mice were treated with either vehicle or RS—Z thirty minutes after the LPS challenge. Mice in group 1 (control) and Group 2 (LPS challenged) were vehicle (0.25% CMC) treated intraperitoneally (i.p.). Mice in Group 3 were treated with RS—Z at a dose of 0.1 mg/kg body weight by i.p. injection. Mice in Group 4 were treated with RS—Z at a dose of 1.0 mg/kg body weight by i.p. injection. Group 5 were treated with RS—Z at a dose of 10 mg/kg body weight by i.p. injection.

Example 23

RS—Z Reduces Neutrophils in Bronchoalveolar Lavage (BAL) Fluid

Mice were sacrificed three hrs after the LPS challenge using an overdose of sodium pentothal (100 mg/kg, i.p.). The trachea were cannulated and 0.5 ml of PBS (phosphate buffered saline) was used for lavage at a time and this step was repeated three times. About 1.5 ml of BAL fluid was recovered per mouse. The BAL fluid was centrifuged ($400 \times g$, 4° C., 6 min) and the supernatant was kept at −70° C. until analyzed for biochemical parameters. The BAL cells were washed three times with PBS and the pellet was resuspended in 200 μl cold PBS. For total cell counts, BAL cell suspension was diluted 1:20 in PBS and cells were counted in a hemocytometer. For differential counts, BALF cell suspension smear was made on glass slides followed by Leishman's stain. The cells were identified and counted by standard methodology. At least 300 cell (all types) per slide were counted and the percentage of neutrophils was calculated.

Example 24

RS—Z Reduces the Lung Injury Score in Mice

The excised lung portions from all the groups was fixed in 10% Buffered formalin. The fixed tissue was embedded in paraffin, sectioned into 4 μm and stained with haematoxylin-eosin for observation under the light microscope. The injury was scored with a semi-quantitative grading system based on the structure changes edema, alveolar and interstitial hemorrhage and inflammatory cells sequestration (Matthay M A, Zimmerman G A, Esmon C, Bhattacharya J, Caller B, et al. (2003) Future research directions in acute lung injury: Summary of a National Heart, Lung, and Blood Institute working group. Am J Respir Crit. Care Med 167: 1027-1035). Semi-quantitative grading system was a 0-to-4 point grading system: 0=No injury, 1=25% injury in a light microscope field, 2=50% injury in a light microscope field, 3=75% injury in a light microscope field, 4= almost 100% injury in a light microscope field. Five light microscopic fields were analyzed for a particular pathological specimen to determine mice lung injury score.

Advantages of the Invention

1. The present invention provides novel anti-inflammatory lead compounds.
2. This novel molecule can be used to develop new drugs for treating various inflammatory diseases of humans.
3. The compounds of present invention are useful as an active ingredient of anti-inflammatory medicament of acute lung injury or related conditions like ARDS.

We claim:
1. A compound of general formula 1

General Formula 1 wherein
$R_1$=H,
$R_2$=COOMe,
$R_3$=$(CH_2)_n COOR_4$,
$R_4$=$C_2H_5$, $C_3H_7$, $C_4H_9$, $C_5H_{11}$, or $C_6H_{11}$, and
n=1-7;
or wherein the compound is selected from the group consisting of

3-(2-pyridylthio) propionic acid butyl ester (RS20), 3-(2-pyridylthio) propionic acid pentyl ester (RS Z), 7-(2-pyridylthio) heptanoic acid ethyl ester (RS 32), and 3-(2-pyridylthio) propionic acid cyclohexyl ester (RS 21).

2. The compound as claimed in claim 1, wherein the compound is selected from the group consisting of

3-(2-pyridylthio) propionic acid butyl ester (RS20);

3-(2-pyridylthio) propionic acid pentyl ester (RS Z);

7-(2-pyridylthio) heptanoic acid ethyl ester (RS 32);

3-(2-pyridylthio) propionic acid cyclohexyl ester (RS 21);

2-(2-pyridylthio)-hexanedioic acid 6-cyclohexyl ester 1-methyl ester (AD 21);

2-(2-pyridylthio)-hexanedioic acid 1-methyl ester 6-propyl ester (AD 20);

2-(2-pyridylthio)-hexanedioic acid-1-methyl ester 6-pentyl ester (AD Z); and 2-(2-pyridylthio)-decanedioic acid-1O-ethyl ester 1-methyl ester (AD 32).

3. The compound as claimed in claim 1, wherein said compound is useful as anti-inflammatory agent.

4. A process for the preparation of the compound of claim 1, wherein said process comprising the steps of:
   i. providing a barton ester of formula IV;

(IV)

wherein
R is $-CH_2CH_2COOC_4H_9$, $-CH_2CH_2COOC_5H_{11}$, $-(CH_2)_6COOEt$, $-CH_2CH_2COOC_6H_{11}$, or $-C(R_1)(R_2)(R_3)$, wherein $R_1=H$, $R_2=COOMe$, $R_3=(CH_2)_nCOOR_4$, $R_4=C_2H_5$, $C_3H_5$, $C_3H_7$, $C_4H_9$, $C_5H_{11}$, or $C_6H_{11}$, and n=1-7;

ii. diluting the barton ester as provided in step (i) with a solvent up to 25 ml;

iii. irradiating the diluted barton ester under sun light at temperature in the range of 15 to 30° C. for period in the range of 15 to 20 minutes;

iv. optionally irradiating the diluted barton ester with olefin under sun light at temperature in the range of 25 to 30° C. for period in the range of 15 to 20 minutes;

v. removing the solvent from the irradiated solution as obtained in step (iv) under reduced pressure in the range of 30 to 50 millibar to obtain an oily crude product; and vi. purifying crude product as obtained in step (v) by preparative TLC to obtain the compound of claim 1.

5. The process as claimed in claim 4, wherein solvent used in step (ii) is dry or degassed benzene or $CH_2Cl_2$.

6. The process as claimed in claim 4, wherein olefin used in step (iv) is methyl acrylate.

7. The process as claimed in claim 1, wherein step (iii) uses an electric bulb of 200 watt to irradiate the solution for period in the range of 8 to 10 hrs.

8. The compound as claimed in claim 1, wherein said compounds exhibiting inhibition of the LPS induced ICAM-1 (Intercellular cell adhesion molecule-1) expression and neutrophil adhesion on human endothelial cells with $IC_{50}$ in the range of 50+0.84 to 178±0.81 µM and 61±0.84 to 94±0.92 µM respectively.

9. The compound as claimed in claim 2, wherein compound RS—Z exhibiting reduction of the neutrophil influx in the lungs in a mice model of acute lung injury at doses of 0.1, 1.0 and 10 mg/kg b. wt. i.p. and attenuation of the LPS-induced lung injury in mice at doses of 0.1. 1.0 and 10 mg/kg body weight, i.p.

* * * * *